US008071340B1

(12) United States Patent
Nadeau et al.

(10) Patent No.: US 8,071,340 B1
(45) Date of Patent: Dec. 6, 2011

(54) BIOCATALYTIC PROCESS FOR THE PRODUCTION OF ORTHO-AMINOPHENOLS FROM CHLORAMPHENICOL AND ANALOGS

(75) Inventors: Lloyd J. Nadeau, Mexico Beach, FL (US); Heather R. Luckarift, Port St Joe, FL (US); Jim C. Spain, Atlanta, GA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 1309 days.

(21) Appl. No.: 11/602,435

(22) Filed: Nov. 2, 2006

Related U.S. Application Data

(60) Provisional application No. 60/735,643, filed on Nov. 10, 2005.

(51) Int. Cl.
*C12P 13/00* (2006.01)

(52) U.S. Cl. ......... 435/128; 435/189; 435/191; 435/193

(58) Field of Classification Search .................. 435/128, 435/189, 191, 193
See application file for complete search history.

(56) References Cited

U.S. PATENT DOCUMENTS 6,797,497 B1 * 9/2004 Spain et al. .................... 435/128
7,364,881 B1 * 4/2008 Nadeau et al. ................ 435/128

OTHER PUBLICATIONS

Nishino et al. Appl. Environmental Microbiol. (1993) 59(8): 2520-2525.*

M.D. Corbett et al., "Synthesis and Antibiotic Properties of Chloramphenicol Reduction Products", Antimicrobial Agents and Chemotherapy, Feb. 1978, p. 193-198, vol. 13, No. 2.

J.K. Davis et al., "Sequence Analysis and Initial Characterization of Two Isozymes of Hydroxylaminobenzene Mutase from *Pseudomonas pseudoalcaligenes* JS45", Applied and Environmental Microbiology, Jul. 2000, p. 2965-2971, vol. 66, No. 7.

V. Kadiyala et al., "Construction of *Escherichia coli* Strains for Conversion of Nitroacetophenones to *ortho*-Aminophenols", Applied and Environmental Microbiology, Nov. 2003, p. 6520-6526, vol. 69, No. 11.

H. Kaseda et al., "Biosynthetic Routes to 2-Aminoacetophenone and 2-Amino-3-hydroxyacetophenone", J. Biochem, 1973, vol. 74, No. 1, p. 127-133.

H. Luckarift et al., "Continuous Synthesis of Aminophenols from Nitroaromatic Compounds by Combination of Metal and Biocatalyst", Chem. Commun., 2005, p. 383-384.

H. Luckarift et al., "Enzyme Immobilization in a Biomimetic Silica Support", Nature Biotechnology, Jan. 2004, p. 1-3.

L.J. Nadeau et al., "Production of 2-Amino-5-Phenoxyphenol from 4-Nitrobiphenyl Ether Using Nitrobenzene Nitroreductase and Hydroxylaminobenzene Mutase from *Pseudomonas pseudoalcaligenes* JS45", Journal of Industrial Microbiology & Biotechnology, 2000, p. 301-305, vol. 24.

C.C. Somerville et al., "Purification and Characterization of Nitrobenzene Nitroreductase from *Pseudomonas pseudoalcaligenes* JS45", Journal of Bacteriology, Jul. 1995, p. 3837-3842, vol. 177, No. 13.

* cited by examiner

*Primary Examiner* — Susan Hanley
(74) *Attorney, Agent, or Firm* — AFMCLO/JAZ; Bart S Hersko

(57) ABSTRACT

A process for the production of ortho-aminophenolic analogs of chloramphenicol using a biocatalyst consisting of pure enzymes, partially purified enzymes, cell lysate, intact cells, or a metal reaction linked with a subsequent enzymatic reaction. The biocatalyst is an enzyme system that makes use of a nitroreductase enzyme that initially reduces the nitroarene to the hydroxylaminoarene and a mutase enzyme that converts the hydroxylaminoarene to an ortho-aminophenol. The biocatalyst can also consist of a coupled, two-step metal and enzyme reaction in which the metal, such as zinc, catalyzes the transformation of the nitroarene to the hydroxylaminoarene and the mutase then catalyzes the transformation of hydroxylaminoarene to the corresponding ortho-aminophenol.

7 Claims, 2 Drawing Sheets

BIOCATALYTIC PROCESS FOR THE PRODUCTION OF ORTHO-AMINOPHENOLS FROM CHLORAMPHENICOL AND ANALOGS

CROSS REFERENCE TO RELATED APPLICATION

This application claims priority to the filing date of Provisional Application Ser. No. 60/735,643, filed Nov. 10, 2005, the entire contents of which are hereby incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates to production of novel ortho-aminophenol analogs from chloramphenicol, and related substrate analogs.

Ortho-aminophenols are intermediates in the synthesis of polybenzoxazole polymers and biologically active compounds such as common phenoxazinones that exhibit antimicrobial properties. Microbes constantly acquire resistance to antibiotics; therefore, new antibiotics are required to combat the pathogenic strains of bacteria.

The common route for commercial chemical synthesis of aminophenols occurs in two steps, nitration of phenol followed by reduction of the nitro-group with a metal to make the amine. The influence of the hydroxyl moiety varies with each substrate. For example, for phenol the substitution is directed preferentially to the ortho-position, but for naphthalene the para-position is more readily attacked. In either case, yields are very low for mononitration of phenols and conditions needed are extreme.

Although, the use of whole cells is limited by the toxicity of the antibiotic substrate, the use of free enzymes obtained from microbes, such as the nitrobenzene reductase is employable if a continuous supply of the cofactor, NADPH, for catalytic activity is provided. The activity of nitrobenzene reductase and hydroxylaminobenzene (HAB) mutase in concert can be exploited to catalyze the conversion of a range of nitroaromatic compounds to yield novel ortho-aminophenols. Additionally, nitrobenzene can be reduced to HAB by a zinc-catalyzed chemical reduction reaction and a subsequent reaction containing the HAB mutase also yields novel ortho-aminophenols. However, the activity of enzymes and metal reactants are often optimal under dissimilar conditions, and so their combination in a single reaction system is often a limitation. Therefore, the use of sequential metal reaction and biocatalysts has recently started to receive attention and a few reports demonstrate the applicability of the approach. For example, the combined action of an immobilized glucose isomerase and a copper catalyst was reported for the conversion of D-glucose to D-mannitol. Encapsulated lipase enzymes are also reported in 'one-pot' reactions with rhodium catalysts for esterification and C-C bond hydrogenation reactions.

Accordingly, it is an object of the present invention to couple a zinc chemical reaction and the HAB mutase enzymatic reaction for the continuous conversion of chloramphenicol, and its analogs to produce aminophenol analogs.

Other objects and advantages of the invention will be set forth in part in the description which follows, and in part will be obvious from the description, or may be learned by practice of the invention. The objects and advantages of the invention may be realized and attained by means of the methods and combinations particularly pointed out in the appended claims.

SUMMARY OF THE INVENTION

In accordance with the present invention there is provided a process for the production of ortho-aminophenols from chloramphenicol and related analogs (e.g., chloramphenicol palmitate and chloramphenicol pantothenate) by using a biocatalyst consisting of pure enzymes, partially purified enzymes, cell lysate or immobilized enzyme in combination with a metal that catalyses a reduction reaction. One biocatalytic scheme provides an enzyme system that makes use of a nitroreductase that catalyzes the enzymatic reduction of a nitroarene to the hydroxylaminoarene. Another biocatalyst is an enzyme system that makes use of a mutase enzyme that converts the hydroxylaminoarene to an ortho-aminophenol. Various bacteria produce this mutase enzyme and can be used as the source(s) for the enzymes. In an alternate scheme, the biocatalyst consists of a coupled, two-step metal and enzyme reaction in which a metal, such as zinc, catalyzes the transformation of the nitroarene to the hydroxylaminoarene and the mutase then catalyzes the transformation of the hydroxylaminoarene to the corresponding ortho-aminophenol.

The reaction scheme for the conversion of chloramphenicol to the aminophenol analog can be represented as follows:

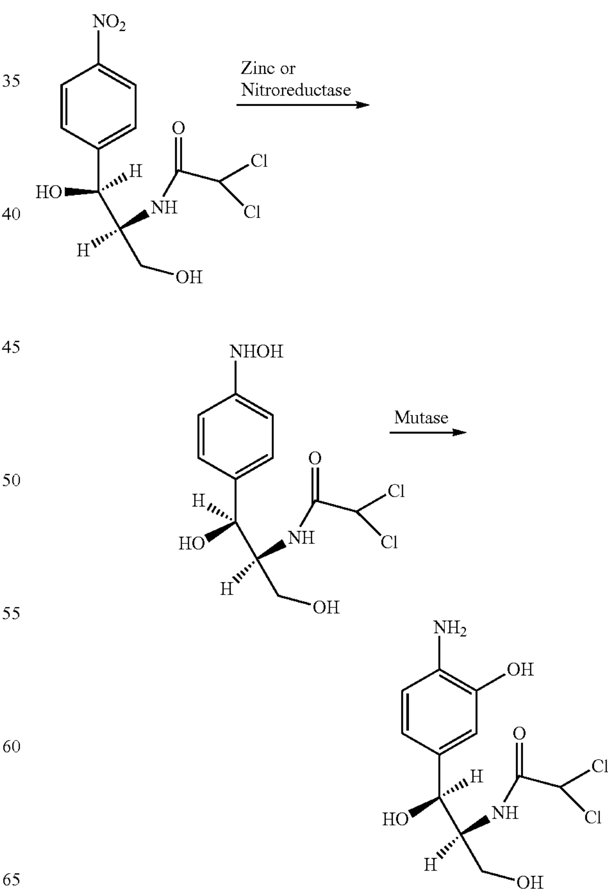

The example given serves to explain the embodiment of the present invention. The example is not to be construed as being exhaustive as to the scope of this invention. The invention and this further relates to the conversion of a chloramphenicol analogs e.g. chloramphenicol palmitate and chloramphenicol pantothenate.

DETAILED DESCRIPTION OF THE INVENTION

Figure 1:
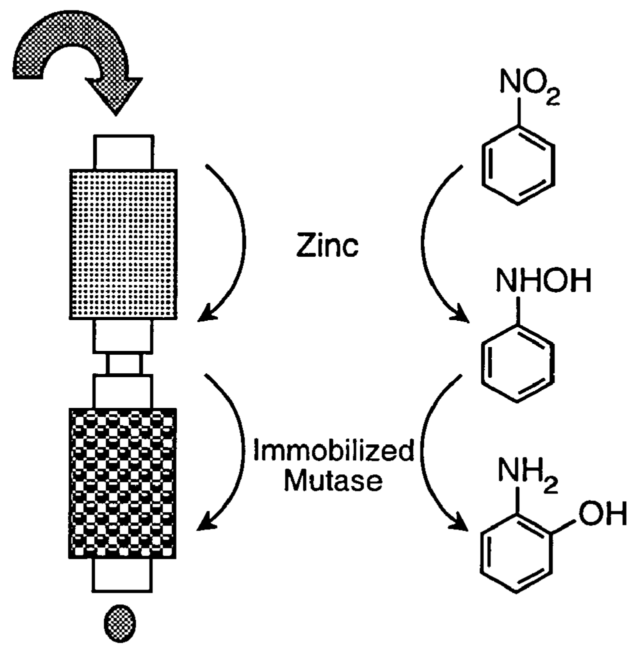
FIG. 1 illustrates the transformation of nitrobenzene to 2-aminophenol in the continuous flow system.

The process of this invention can be carried out as a batch process or as a continuous process. As noted previously, the process uses a nitroreductase and mutase to convert nitroarenes, such as chloramphenicol, to the ortho-aminophenol. Furthermore the process can involve metal reaction linked with a subsequent enzymatic reaction consisting of pure enzymes, partially purified enzymes, and cell lysate. Transformation of the nitroarene to the hydroxylaminoarene is catalyzed by a metal, such as zinc, after which the mutase then catalyzes the transformation of hydroxylaminoarene to the corresponding ortho-aminophenol.

Partial Purification of the Enzymes

*Pseudomonas pseudoalcaligenes* strain JS45 was grown and crude cell extracts were prepared as described by Nishino and Spain, Degradation of nitrobenzene by a *Pseudomonas pseudoalcaligenes*, Appl. Environ. Microbiol., 59: 2520-2525 (1993), incorporated herein by reference. The nitrobenzene nitroreductase was purified as described by Somerville, Nishino, and Spain, Purification and characterization of nitrobenzene nitroreductase from *Pseudomonas pseudoalcaligenes* JS45, J. Bacteriol., 177: 3837-3842 (1995), incorporated herein by reference. The crude extract was loaded on a 100 ml Q-Sepharose Fast Flow column (Pharmacia, XK-26) previously equilibrated with 150 mM KCl in 20 mM phosphate buffer. Proteins were eluted with a step gradient that began with 100 ml buffer containing KCl (150 mM) and then a linear gradient of 150 to 300 mM KCl at a flow rate of 2.5 ml/minute. The fractions containing nitrobenzene nitroreductase activity, which eluted in the linear gradient between 65 to 80 ml, were pooled, washed three times and concentrated on an Amicon PM-10 membrane and stored in 500 μl aliquots at −80° C. for use in transformation assays.

The HabA mutase was cloned into *E. coli* as described by Davis, J. K., G. C. Paoli, Z. He, L. J. Nadeau, C. C. Somerville, and J. C. Spain. 2000, Sequence analysis and initial characterization of two isozymes of hydroxylaminobenzene mutase from *Pseudomonas pseudoalcaligenes* JS45 Appl. Environ. Microbiol. 66:2965-2971, incorporated herein by reference. The enzyme was purified from *E. coli* JS995 essentially as described by Paoli and Spain: *E. coli* derived from *Pseudomonas pseudoalcaligenes* JS45: Solubilization and purification of membrane associated hydroxylaminobenzene mutase, 61, Oct. 2-6, 2001 ASM Conference on Biodegradation, Biotransformation, and Biocatalysis in, San Juan, Puerto Rico, incorporated herein by reference.

*E. coli* JS995, a recombinant organism expressing HabA from *Pseudomonas pseudoalcaligenes* JS45, was cultured at 37° C. in Luria-Bertani medium (1 Liter) containing ampicillin (100 mg/liter) to maintain plasmid selection. The culture was induced with 0.7 mM IPTG (isopropyl-beta-D-thiogalacto pyranoside) for approximately 12 hours. Cultures were harvested by centrifugation, washed and suspended in buffer [50 mM MES (2-[N-morpholino]ethanesulfonic acid), 0.15 M NaCl, pH 7.0] and broken by three passages though a French pressure cell. The cell debris was removed by centrifugation (12,000×g, 15 minutes, 4° C.) and the soluble and membrane fractions separated by ultra-centrifugation (100,000×g, 1 hour, 4° C.). The membrane pellet was suspended in buffer (50 mM MES, 0.15 M NaCl, 2% n-octyl-β-D-glucopyranoside, pH 7.0), homogenized with a tissue grinder and stirred for 30 minutes at 4° C. $MgCl_2$ was added to a final concentration of 50 mM, mixed briefly and heated at 55° C. for 5 minutes. The resulting solubilized membrane was then clarified by ultra-centrifugation (100,000×g, 1 hour, 4° C.) and stored at −80° C. In a typical purification, the specific activity of the partially purified HAB mutase A was 3.5 μmol/minute/mg total protein.

Chemicals

Chloramphenicol, nitrobenzene, ammonium chloride and zinc dust were obtained from Sigma-Aldrich (St. Louis, Mo.). Hydroxylaminobenzene was synthesized according to the method of Furniss, Hannaford, Smith, and Tatchell, Vogel's Textbook of Practical Organic Chemistry, John Wiley & Sons, New York, 1989, incorporated herein by reference.

Continuous Flow Experiments

For continuous flow experiments, a 10 ml Pharmacia Biotech column was packed with 5 g Zinc (40 mesh) and 5 g sand and a second 10 ml column attached in sequence contained 5 ml mutase immobilized in biomimetically-derived silica (biosilica) as described in Luckarift, H. L., L. J. Nadeau, and J. C. Spain, 2005, Continuous synthesis of aminophenols from nitroaromatic compounds by combination of metal and biocatalyst Chem. Commun. 3:383-384, incorporated herein by reference. Substrate was pumped through the system at a fixed flow rate and the eluate collected for analysis. The entire apparatus was maintained in an incubator at 30° C. Substrates were dissolved in water containing $NH_4Cl$ (40 mM) and sparged with argon to ensure an anaerobic environment. Biosilica immobilization was performed as described previously.

Batch Transformation

Batch transformations of chloramphenicol to the ortho-aminophenol were performed by dissolving chloramphenicol (0.323 g) in water (130 ml) containing ammonium chloride (0.1 g) with continuous stirring at 40° C., essentially as described previously. The reaction was initiated by adding zinc dust (0.26 g), and the reduction reaction was monitored by high performance liquid chromatograph (HPLC), as described below. The zinc was pelleted by centrifugation and supernatant was buffered with phosphate buffer (20 mM final). Subsequently, mutase A (0.97 mg) was added to convert the hydroxylamino-chloramphenicol to the aminophenol-chloramphenicol (N-[2-(4-Amino-3-hydroxy-phenyl)-2-hydroxy-1-hydroxymethyl-ethyl]-2,2-dichloro-acetamide), and transformation was monitored by HPLC.

Analytical Methods

An HPLC equipped with a diode array detector monitoring $A_{210}$ (Hewlett-Packard, Model 1040M, Wilminutegton Del.) was used to identify and quantify the nitroarenes and corresponding aminophenols. Reactants and products of nitrobenzene conversion were monitored by reverse-phase HPLC on a Supelco ABZ column with an acetonitrile/water (+0.1% trifluoroacetic acid) gradient. Reactants and products of chloramphenicol transformation were resolved by ion pairing chromatography on a Luna C18 (Phenomenex) column with an acetonitrile/triethylamine (10 mM, adjusted to pH5 with acetic acid) gradient. LC-MS analysis was performed with an LCQ Mass Spectrometer (ThermoFinnigan) equipped with an atmospheric pressure chemical ionization (APCI) interface in negative mode with the following parameters; vaporizer temperature, 450° C.; capillary temperature, 200° C.; sheath gas, 20; aux gas, 40; source current, 80 μA; source voltage, ~4 kV; capillary voltage, −33 V (APCI); and tube lens voltage, 15 V. LC-MS Analytes were separated on a Luna C18 column (150×2 mm, Phenomenex) with an acetonitrile/water gradient at 0.3 ml/minute.

Nitrobenzene nitroreductase activity was measured spectrophotometrically by following NADPH oxidation as previously described. Mutase enzyme activity was determined as described previously.

$^{13}C$ and $^{1}H$ NMR data for N-[2-(4-Amino-3-hydroxy-phenyl)-2-hydroxy-1-hydroxymethyl-ethyl]-2,2-dichloro-acetamide was obtained by dissolving the sample in DMSO. NMR spectra were recorded on a Varian (nova spectrometer equipped with a 5 mm indirect detection probe, operating at 500 MHz for $^{1}H$ and at 125 MHz for $^{13}C$, as performed by Dr. Ion Ghiviriga, University of Florida.

The following examples illustrate the invention:

Example 1

Chemical Reaction Coupled to an Enzymatic Reaction to Produce Aminophenol from Nitrobenzene The biological and chemical reduction of a nitroaromatic compound to a hydroxylaminoarene occurs by the transfer of four electrons and protons:

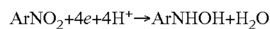

$$ArNO_2+4e+4H^+ \rightarrow ArNHOH+H_2O$$

Hydroxylaminoarenes can be chemically synthesized from nitroaromatic compounds by using metals, such as zinc, in the presence of ammonium sulfate. For example, hydroxylaminobenzene is readily synthesized in an aqueous solution containing ammonium chloride and 2 moles of zinc per mole of nitrobenzene.

Applicants used a method of enzyme immobilization in biomimetically-derived silica (biosilica) that increases the general mechanical stability of enzymes and facilitates their application in flow-through reactor systems as described by Luckarift, H. L., J. C. Spain, R. R. Naik, and M. O, Stone. 2004, Enzyme immobilization in biomimetic slica support. Nature Biotech. 22 (2):211, incorporated herein by reference. Here, Applicants have determined the suitability of biosilica as an immobilization matrix with the HAB mutase enzyme to convert the hydroxylamino arene to the corresponding aminophenol. FIG. 1 illustrates the transformation of nitrobenzene to 2-aminophenol in the continuous flow system.

Figure 2:
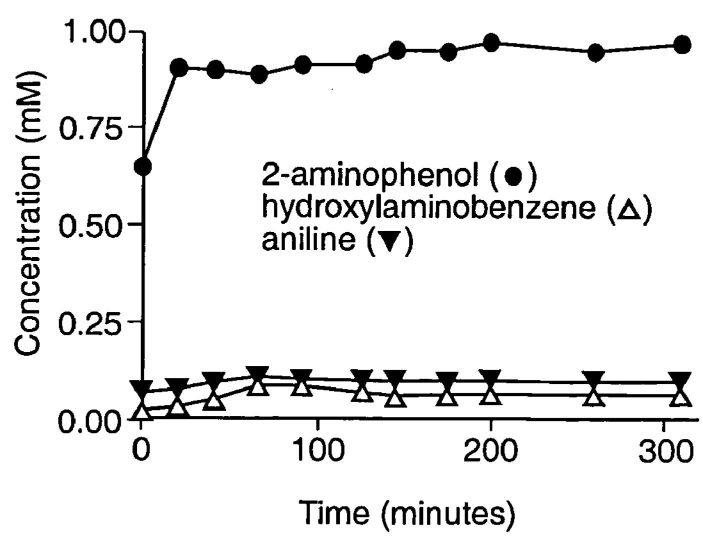
FIG. 2 illustrates the transformation of nitrobenzene to ortho-aminophenol by a sequential zinc-reduction and mutase-catalyzed reaction system.

In initial studies, Applicants used the natural substrate to develop the process illustrated in FIG. 1, and to demonstrate a system useful for conversion of chloramphenicol and its analogs. The activity of the HAB mutase enzyme entrapped in biosilica was compared with that of the free enzyme to determine whether the enzymes were active in their entrapped form. Following immobilization, 78% of the initial free enzyme activity was detected in the biosilica nanospheres. The immobilized mutase enzyme (5 ml biosilica containing 0.25 mg enzyme) was incorporated into a column and connected in series to a second column containing 5 g of zinc which had been pre-equilibrated with a solution of nitrobenzene for at least 2 column volumes. When 1 mM nitrobenzene was pumped through the two columns at a flow rate of 0.25 ml/minute, the corresponding 2-aminophenol (0.89 mM±0.095) was obtained continuously for over 300 minutes demonstrating a conversion efficiency of 83.67% (±1.45) (FIG. 2). FIG. 2 illustrates the transformation of nitrobenzene to 2-aminophenol by a sequential zinc/mutase catalysed reaction system; 2-aminophenol (•), hydroxylaminobenzene (Δ), aniline (▼).

Small quantities of HAB (66 μM±22) and aniline (97 μM±13) (byproduct of the zinc reaction) were detected throughout the reaction (FIG. 2). The flow rate and substrate concentration were increased to 0.5 ml/minute and 5 mM, 3.56 mM (±0.24) 2-aminophenol was produced for over 500 minutes with no loss in activity indicating a conversion efficiency of 73.72% (±5.83). 0.89 mM (±0.31) of hydroxylaminobenzene, aniline (0.37 mM±0.07) and nitrosobenzene (0.025 mM±0.024) were detected.

The results suggested that the capacity of the mutase column was exceeded at the higher flow rate. In these preliminary investigations, no attempt was made to optimize column configurations and flow rates. The efficiency of the mutase column alone was investigated by feeding 1 mM HAB through the column at fixed flow rates. However, the hydroxylaminobenzene was unstable and susceptible to auto-oxidation, which made quantification of the conversion efficiency difficult. One of the advantages to a continuous reaction system is the instantaneous conversion of the unstable HAB intermediate into 2-aminophenol before auto-oxidation can occur.

Example 2

Batch Chemical Reaction Followed by an Enzymatic Reaction to Produce N-[2-(4-Amino-3-Hydroxy-Phenyl)-2-Hydroxy-1-Hydroxymethyl-Ethyl]-2,2-Dichloro-Acetamide from Chloramphenicol The biosynthesis of antibiotics using intact bacterial cells is inherently limited by auto-inhibition due to the biocidal properties of the product. The use of metals and enzyme reaction systems therefore provides an attractive alternative. The chemical reduction of the nitroarene to the hydroxylaminoarene by using zinc in a batch process has been previously described. The use of the zinc/mutase sequential reactions were therefore investigated with the antibiotic chloramphenicol (N-[2-hydroxy-1-(hydroxymethyl)-2-(4-nitrophenyl)ethyl]-2,2-dichloro-acetamide) as a model system.

Preliminary investigation demonstrated that the nitro group of chloramphenicol was reduced to a hydroxylamino-chloramphenicol derivative by reaction with zinc and the identity of the product was confirmed by LC-MS analysis.

Subsequently, batch reduction of chloramphenicol was performed, in duplicate, as described above. The mutase incubated in the presence of the hydroxylamino-chloramphenicol converted the reduction product to the ortho-aminophenolic chloramphenicol. Recovery of the aminophenol, N-[2-(4-Amino-3-hydroxy-phenyl)-2-hydroxy-1-hydroxymethyl-ethyl]-2,2-dichloro-acetamide, from ethyl acetate extraction was 60 and 85%. The aminophenol-chloramphenicol product was purified from this reaction by LC, and used as a product standard in subsequent investigations.

Figure 3:
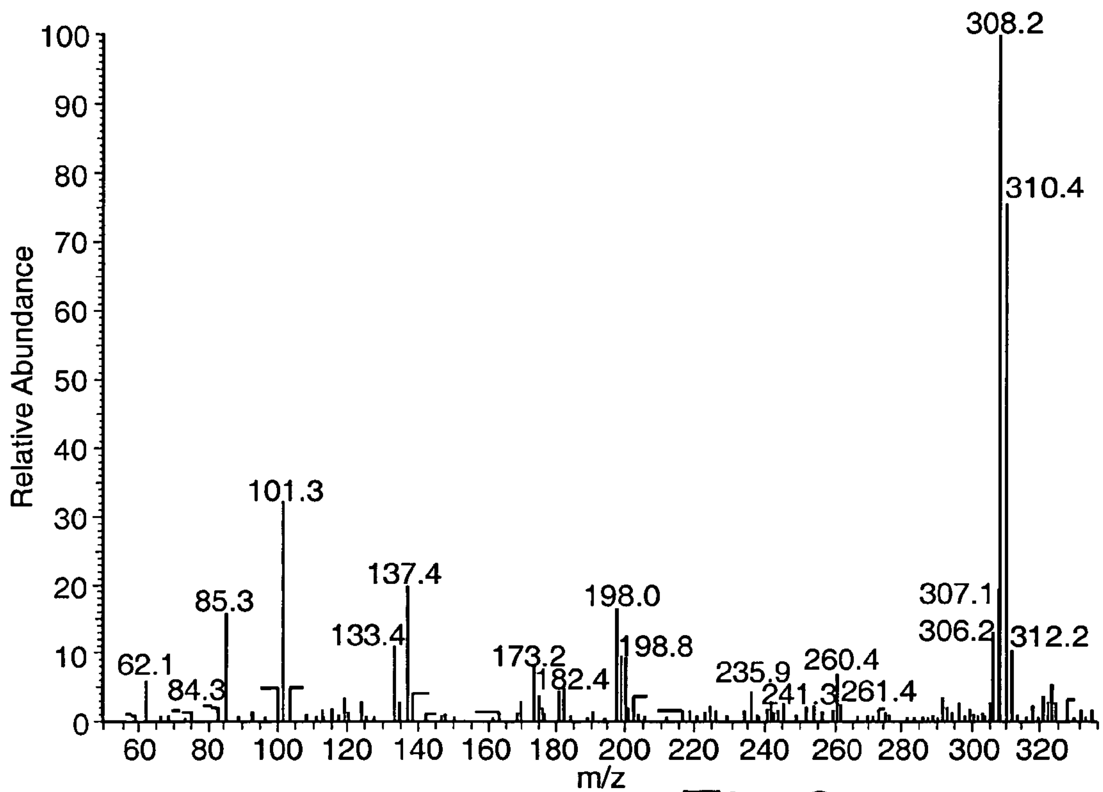
FIG. 3 illustrates the LC-MS analysis of the ortho-aminophenolic chloramphenicol, N-[2-(4-Amino-3-hydroxy-phenyl)-2-hydroxy-1-hydroxymethyl-ethyl]-2,2-dichloro-acetamide, formed from chloramphenicol.
Figure 4:
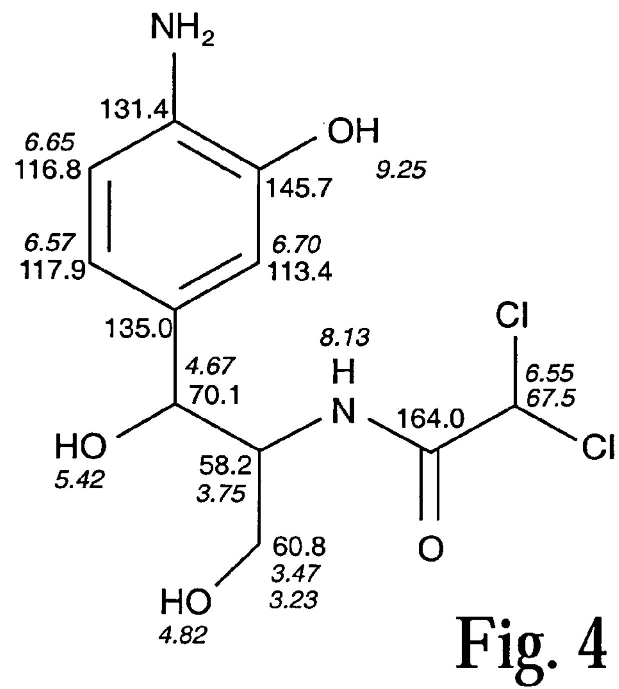
FIG. 4 illustrates the $^{13}C$ and $^{1}H$ NMR data for N-[2-(4-Amino-3-hydroxy-phenyl)-2-hydroxy-1-hydroxymethyl-ethyl]-2,2-dichloro-acetamide, formed from chloramphenicol by sequential enzymatic reactions and by sequential zinc-enzymatic reactions.

FIG. 3 illustrates the LC-MS analysis of the ortho-aminophenolic chloramphenicol, N-[2-(4-Amino-3-hydroxy-phenyl)-2-hydroxy-1-hydroxymethyl-ethyl]-2,2-dichloro-acetamide, formed from chloramphenicol. FIG. 4 illustrates the $^{13}C$ and $^{1}H$ NMR data for N-[2-(4-Amino-3-hydroxy-phenyl)-2-hydroxy-1-hydroxymethyl-ethyl]-2,2-dichloro-acetamide, formed from chloramphenicol by sequential enzymatic reactions and by sequential zinc-enzymatic reactions.

The success of the small scale batch reaction of chloramphenicol led Applicants to investigate the large scale synthesis of this product using the continuous zinc/mutase column system as described for the nitrobenzene model system, and as described in Example 3 below.

Example 3

Chemical Reaction Coupled to an Enzymatic Reaction to Produce Aminophenol Analog from Chloramphenicol The zinc/mutase column system was used as described for the nitrobenzene model system (FIG. 1). When an aqueous solution of chloramphenicol (1 mM) was pumped through the two columns at a flow rate of 0.25 ml/minute, the corresponding aminophenolic analog (0.94 mM±0.11) was obtained continuously for 24 hours (94% conversion efficiency). Degeneration of the zinc column was observed over time and was detected by the formation of a white zinc oxide precipitate and a nitroso intermediate of chloramphenicol, which was detected by HPLC. The zinc column was replaced and the system continued for a further 24 hours with a conversion efficiency of 89%. This demonstrates the stability of the immobilized mutase enzyme and its utility for continuous production of the aminophenolic-chloramphenicol.

Example 4

Production of Aminophenolic Chloramphenicol Using Purified Enzymes and Cell Lysates Chloramphenicol was incubated in the presence of purified nitroreductase and NADPH which resulted in the production of one compound with spectral characteristic and retention time analogous to the reduction product formed using zinc. This one compound was previously identified as the hydroxylamino-chloramphenicol. Incubation of mutase A with the hydroxylamino intermediate resulted in production of the aminophenolic chloramphenicol.

Chloramphenicol incubated in the presence of cell lysate of recombinant *E. coli* expressing both nitroreductase and mutase yielded one product with spectral characteristic and retention time to that described above. This end product was characterized and identified as the aminophenolic-chloramphenicol.

Having thus described exemplary embodiments of the present invention, it should be noted by those skilled in the art that the disclosures herein are exemplary only and that alternatives, adaptations and modifications may be made within the scope of the present invention.

We claim:

1. A process for the production of an ortho-aminophenol from a nitroarene comprising reacting a biocatalyst consisting of a nitroreductase enzyme that initially reduces said nitroarene to the corresponding hydroxylaminoarene and a mutase enzyme that converts said hydroxylaminoarene to said ortho-aminophenol, and recovering a fraction containing said ortho-aminophenol, wherein said nitroarene is selected from the group consisting of chloramphenicol, chloramphenicol palmitate, chloramphenicol pantothenate, and mixtures thereof.

2. The process of claim 1, wherein said nitroarene is a compound of the formula:

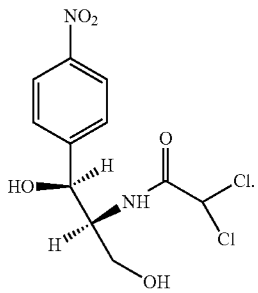

3. The process of claim 2 wherein said ortho-aminophenol is N-[2-(4-amino-3-hydroxy-phenyl)-2-hydroxy-1-hydroxymethyl-ethyl]-2,2-dichloro-acetamide.

4. A process for the production of an ortho-aminophenol from a nitroarene which comprises reacting said nitroarene with a metal catalyst to obtain the corresponding hydroxylaminoarene and reacting said hydroxylaminoarene with a biocatalyst consisting of a mutase enzyme that converts said hydroxylaminoarene to said ortho-aminophenol, and recovering a fraction containing said ortho-aminophenol wherein said nitroarene is selected from the group consisting of chloramphenicol, chloramphenicol palmitate, chloramphenicol pantothenate, and mixtures thereof.

5. The process of claim 4, wherein said nitroarene is a compound of the formula:

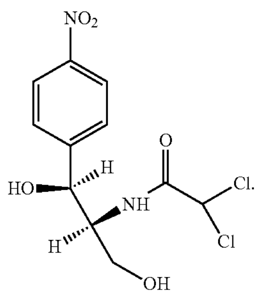

6. The process of claim 5 wherein said metal catalyst is zinc.

7. The process of claim 5 wherein said ortho-aminophenol is N-[2-(4-amino-3-hydroxy-phenyl)-2-hydroxy-1-hydroxymethyl-ethyl]-2,2-dichloro-acetamide.

* * * * *